US012233104B2

(12) United States Patent
Charych et al.

(10) Patent No.: US 12,233,104 B2
(45) Date of Patent: Feb. 25, 2025

(54) COMBINATION OF AN IL-2RBETA-SELECTIVE AGONIST AND A LONG-ACTING IL-15 AGONIST

(71) Applicant: Nektar Therapeutics, San Francisco, CA (US)

(72) Inventors: Deborah H. Charych, Albany, CA (US); Peter Benedict Kirk, Oxfordshire (GB)

(73) Assignee: Nektar Therapeutics, San Francisco, CA (US)

( * ) Notice: Subject to any disclaimer, the term of this patent is extended or adjusted under 35 U.S.C. 154(b) by 552 days.

(21) Appl. No.: 15/765,207

(22) PCT Filed: Oct. 7, 2016

(86) PCT No.: PCT/US2016/056088
§ 371 (c)(1),
(2) Date: Mar. 30, 2018

(87) PCT Pub. No.: WO2017/062832
PCT Pub. Date: Apr. 13, 2017

(65) Prior Publication Data
US 2018/0296645 A1 Oct. 18, 2018

Related U.S. Application Data

(60) Provisional application No. 62/239,207, filed on Oct. 8, 2015.

(51) Int. Cl.
*A61K 38/20* (2006.01)
*A61K 47/60* (2017.01)
*A61P 35/00* (2006.01)

(52) U.S. Cl.
CPC ...... *A61K 38/2086* (2013.01); *A61K 38/2013* (2013.01); *A61K 47/60* (2017.08); *A61P 35/00* (2018.01)

(58) Field of Classification Search
None
See application file for complete search history.

(56) References Cited

U.S. PATENT DOCUMENTS

| | | |
|---|---|---|
| 4,401,756 A | 8/1983 | Gillis |
| 4,705,848 A | 11/1987 | Yang et al. |
| 4,766,106 A | 8/1988 | Katre et al. |
| 4,902,502 A | 2/1990 | Nitecki et al. |
| 5,078,997 A | 1/1992 | Hora et al. |
| 5,089,261 A | 2/1992 | Niteck et al. |
| 5,116,943 A | 5/1992 | Koth et al. |
| 5,153,310 A | 10/1992 | Mitchell et al. |
| 5,206,344 A | 4/1993 | Katre et al. |
| 5,419,899 A | 5/1995 | Koths et al. |
| 5,614,185 A | 3/1997 | Koths et al. |
| 5,635,597 A | 6/1997 | Barrett et al. |
| 5,739,208 A | 4/1998 | Harris |
| 5,795,966 A | 8/1998 | Grabstein et al. |
| 5,932,462 A | 8/1999 | Harris et al. |
| 6,034,072 A | 3/2000 | Ralston et al. |
| 6,077,519 A | 6/2000 | Storkus et al. |
| 6,110,721 A * | 8/2000 | Gibbs ............ C12Y 304/21005 435/214 |
| 6,180,095 B1 | 1/2001 | Greenwald et al. |
| 6,706,289 B2 | 3/2004 | Lewis et al. |
| 7,101,965 B2 | 9/2006 | Theze et al. |
| 7,511,094 B2 | 3/2009 | Kozlowski |
| 7,579,439 B2 | 8/2009 | Strom et al. |
| 7,585,837 B2 | 9/2009 | Shechter et al. |
| 9,861,705 B2 | 1/2018 | Bossard et al. |
| 10,960,079 B2 | 3/2021 | Bossard et al. |
| 11,091,525 B2 | 8/2021 | Bossard et al. |
| 2004/0136952 A1 | 7/2004 | Bhaskaran et al. |
| 2004/0175337 A1 | 9/2004 | Richard et al. |
| 2004/0204548 A1 | 10/2004 | Kozlowski et al. |
| 2004/0253587 A1 | 12/2004 | Grabstein et al. |

(Continued)

FOREIGN PATENT DOCUMENTS

| | | |
|---|---|---|
| CN | 101104077 A | 1/2008 |
| EP | 0 473 268 | 3/1992 |

(Continued)

OTHER PUBLICATIONS

Yu et al. (2010, Clin. Cancer Res. 16(24):6019-6028).*
Berge et al., "Pharmaceutical Salts", Journal of Pharmaceutical Sciences, vol. 66, No. 1, pp. 1-19, (Jan. 1977).
Castro et al., "The Basis of Distinctive IL-2- and IL-15-Dependent Signaling: Weak CD122-Dependent Signaling Favors CD8+ T Central-Memory Cell Survival but Not T Effector-Memory Cell Development", The Journal of Immunology, vol. 187, pp. 5170-5182, (2011).
Charyh et al., "NKTR-214, an Engineered Cytokine with Biased IL2 Receptor Binding, Increased Tumor Exposure, and Marked Efficacy in Mouse Tumor Models", Clinical Cancer Research, vol. 22, No. 3, pp. 680-680, (Feb. 1, 2016).
Charych et al., "Tipping the balance in the tumor microenvironment: An engineered cytokine (NKTR-214) with altered IL2 receptor binding selectivity and improved efficacy", Proceedings: AACR 104th Annual Meeting 2013; Apr. 6-10, 2013; Washington, DC. (Abstract #482).

(Continued)

*Primary Examiner* — Elizabeth C. Kemmerer
(74) *Attorney, Agent, or Firm* — Jacqueline F. Mahoney (57) ABSTRACT

In one or more embodiments of the invention, a method is provided, the method comprising the steps of administering to a cancer patient: (a) an IL-2Rβ-activating amount of a long-acting, IL-2Rβ-selective agonist; and (b) an IL-15R-activating amount of a long-acting, IL-15 moiety. In one or more embodiments of the invention, a composition is provided, the composition comprising: an IL-2Rβ-activating amount of a long-acting, IL-2Rβ-selective agonist; and an IL-15R-activating amount of a long-acting, IL-15 moiety. In one or more embodiments of the invention, a kit is provided, the kit comprising: an IL-2Rβ-activating amount of a long-acting, IL-2Rβ-selective agonist; an IL-15R-activating amount of a long-acting, IL-15 moiety; and instructions for use of the IL-2Rβ-selective agonist and the long-acting, IL-15 moiety.

14 Claims, 2 Drawing Sheets

(56) References Cited

U.S. PATENT DOCUMENTS

| | | | |
|---|---|---|---|
| 2005/0014903 | A1 | 1/2005 | Kozlowksi et al. |
| 2005/0069521 | A1* | 3/2005 | Gillies .................. C07K 14/55 424/85.2 |
| 2005/0095223 | A1 | 5/2005 | Sivakumar et al. |
| 2005/0186174 | A1 | 8/2005 | Bossard |
| 2006/0057102 | A1 | 3/2006 | Zheng et al. |
| 2006/0104945 | A1 | 5/2006 | Choi |
| 2006/0257361 | A1* | 11/2006 | Watanabe ......... C07K 14/5443 424/85.2 |
| 2006/0293499 | A1 | 12/2006 | Bentley et al. |
| 2009/0263382 | A1 | 10/2009 | Ewert et al. |
| 2010/0036097 | A1 | 2/2010 | Wittrup et al. |
| 2010/0112607 | A1 | 5/2010 | Varadi et al. |
| 2011/0059042 | A1* | 3/2011 | Nellis ................ C07K 14/5443 424/85.2 |
| 2011/0190209 | A1 | 8/2011 | Culbertson et al. |
| 2014/0328791 | A1 | 11/2014 | Bossard et al. |
| 2015/0017120 | A1 | 1/2015 | Wittrup et al. |
| 2017/0035898 | A1* | 2/2017 | Liu .......................... A61P 35/04 |
| 2018/0085468 | A1 | 3/2018 | Bossard et al. |
| 2019/0008978 | A1 | 1/2019 | Huang et al. |

FOREIGN PATENT DOCUMENTS

| | | |
|---|---|---|
| EP | 0 510 356 A1 | 10/1992 |
| EP | 1 688 146 | 8/2006 |
| JP | 2006-306824 | 9/2009 |
| KR | 10-2009-0103209 | 10/2009 |
| WO | WO 87/00056 A1 | 1/1987 |
| WO | WO 90/12874 A2 | 11/1990 |
| WO | WO 99/45964 A1 | 9/1999 |
| WO | WO 99/60128 A1 | 11/1999 |
| WO | WO 01/62827 A2 | 8/2001 |
| WO | WO 02/00243 A2 | 1/2002 |
| WO | WO 2004/060300 A2 | 7/2004 |
| WO | WO 2004/089280 A2 | 10/2004 |
| WO | WO 2005/000360 A2 | 1/2005 |
| WO | WO 2006/138572 A2 | 12/2006 |
| WO | WO 2007/071388 A1 | 6/2007 |
| WO | WO 2007/075534 A2 | 7/2007 |
| WO | WO 2007/117685 A2 | 10/2007 |
| WO | WO 2008/082613 A2 | 7/2008 |
| WO | WO 2008/082669 A2 | 7/2008 |
| WO | WO 2008/106186 A2 | 9/2008 |
| WO | WO 2009/095479 A2 | 8/2009 |
| WO | WO 2009/139905 A2 | 11/2009 |
| WO | WO 2010/033207 A1 | 3/2010 |
| WO | WO 2012/016131 A1 | 2/2012 |
| WO | WO 2012/065086 A1 * | 5/2012 |
| WO | WO 2013/020079 A2 * | 2/2013 |
| WO | WP 2013/020079 A2 * | 2/2013 |
| WO | WO 2015/125159 A1 | 8/2015 |
| WO | WO 2015/153753 A2 | 10/2015 |

OTHER PUBLICATIONS

Di Sabatino et al., "Role of IL-15 in immune-mediated and infectious diseases", Cytokine & Growth Factor Reviews, vol. 23, pp. 19-33, (2011).
Spaner et al., "Effect of IL-2Rβ-binding cytokines on costimulatory properties of chronic lymphocytic leukaemia cells: implications for immunotherapy", British Journal of Haematology, vol. 127, pp. 531-542, (2004).
Wu, "IL-15 Agonists: The Cancer Cure Cytokine", J. Mol. Genet. Med., vol. 7, pp. 1-6, (Feb. 28, 2014).
PCT International Search Report and the Written Opinion corresponding to PCT Application No. PCT/US2016/056088 date of mailing Jan. 4, 2017.
PCT International Preliminary Report on Patentability corresponding to PCT Application No. PCT/US2016/056088 date of mailing Apr. 19, 2018.
Enzon Pharmaceuticals, Macromolecular Engineering Technologies, 16 pages, (2004).
NEKTAR™—Transforming Therapeutics, Nektar Molecule Engineering: Polyethylene Glycol and Derivatives for Advanced PEGylation, 24 pages, Catalog—2003, (Jul. 2003).
NEKTAR™—Transforming Therapeutics, Nektar Advanced PEGylation: Polyethylene Glycol and Derivatives for Advanced PEGylation, 27 pages, Catalog—2004, (Jul. 2004).
NEKTAR™—Transforming Therapeutics, Nektar Advanced PEGylation: Polyethylene Glycol and Derivatives for Advanced PEGylation, 33 pages, (Catalog 2005-2006).
NOF Corporation, PEG Derivatives, Phospholipid and Drug Delivery Materials for Pharmaceuticals, 46 pages, Catalogue 2003—$1^{st}$, (Jan. 2003).
NOF Corporation, PEG Derivatives, Phospholipid and Drug Delivery Materials for Pharmaceuticals, 27 pages, Catalogue 2003—$2^{nd}$, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
POLYPURE Products, PEG amines; PEG acids and amino acids; PEG thiols and disulfides; BIOTINS, 5 pages, (Apr. 2004).
POLYPURE Products, PEG amines; PEG acids and amino acids; PEG thiols and disulfides; BIOTINS, 5 pages, (Apr. 2005).
Quanta Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producer and provider of monodisperse discrete PEGTM (dPEG™M) derivatives, (Product Catalog), 26 pages, (Updated: Jul. 18, 2005).
Quanta Biodesign, Ltd., Leading innovator, producer and provider of monodisperse discrete PEG™ (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).
European Communication corresponding to European Patent Application No. 16 791 713.7 dated Feb. 25, 2020.
English Translation of Israel Communication corresponding to Israel Patent Application No. 258,456 dated Feb. 13, 2020.
Shibata, et al., "Optimization of protein therapies by polymer-conjugation as an effective DDS", Molecule, vol. 10, No. 1, pp. 162-180, (2005).
Wei, et al., "The CIK cells stimulated with combination of IL-2 and IL-15 provide an improved cytotoxic capacity against human lung adenocarcinoma", Tumor Biology, vol. 35, No. 3, pp. 1997-2007, (2014).
English Translation of Notification of the First Office Action corresponding to Chinese Patent Application No. 201680058497.X date of notification Nov. 30, 2020.
European Communication corresponding to European Patent Application No. 16791713.7-1112 dated Jun. 11, 2020.
English Translation of Notice of Reasons for Rejection corresponding to Japanese Patent Application No. 2018-517898, mailing date Sep. 4, 2020.
Pettit et al., "Structure-Function Studies of Interleukin 15 using Site-specific Mutagenesis, Polyethylene Glycol Conjugation, and Homology Modeling", The Journal of Biological Chemistry, vol. 272, No. 4, Issue of Jan. 24, pp. 2312-2318, (1997).
English Translation of Notification of Second Office Action corresponding to Chinese Patent Application No. 201680058497.X date of notification Jul. 30, 2021.
English Translation of Notice of Fina Rejection corresponding to Japanese Patent Application No. 2018-517898 mailing date Aug. 2, 2021.

(56) References Cited

OTHER PUBLICATIONS

English Translation of 1$^{st}$ Substantive Examination corresponding to Mexican Patent Application No. MX/a/2018/004296 dated Aug. 26, 2021.

* cited by examiner

COMBINATION OF AN IL-2RBETA-SELECTIVE AGONIST AND A LONG-ACTING IL-15 AGONIST

CROSS-REFERENCE TO RELATED APPLICATION

This application is a 35 U.S.C. § 371 application of International Application No. PCT/US2016/056088, filed Oct. 7, 2016, designating the United States, which claims priority to, and the benefit of, U.S. Provisional Patent Application No. 62/239,207 entitled "COMBINATION OF AN IL-2RBETA-SELECTIVE AGONIST AND A LONG-ACTING IL-15 AGONIST", filed Oct. 8, 2015, the contents of which are incorporated by reference herein in their entireties.

FIELD

This invention relates to (among other things) the field of cancer immunotherapy and involves the treatment of an individual suffering from a cancer by administering to the patient a long-acting IL-2Rβ-selective agonist in combination with another pharmacologically active agent.

BACKGROUND

In the context of pharmacological interventions in the treatment of patients suffering from cancer, combination therapies can have many benefits. For example, combination therapies can reduce the development of drug resistance. In addition, combination therapies can be more efficacious (including resulting in increased overall survival) than single agent therapies. Further, when more efficacious, combination treatments can result in fewer overall treatments, thereby resulting in lower treatment costs.

One of the challenges associated with combination therapies is the identification of a combination that is expected to be beneficial.

Administration of IL-2Rβ-selective agonists has been proposed to be beneficial to patients suffering from certain cancers as doing so is expected to reduce the immune-suppressing effects of regulatory T-cells while increasing CD8+ memory T-cells, thereby recruiting the patient's own immune system to eliminate cancer cells. See Charych et al. AACR 2013, Abstract #482.

Recruiting the immune system of the cancer patient in the treatment of cancer via administration of IL-2Rβ-selective agonists—which can be directly immunoactivating—can be further enhanced through the administration of other agents.

As a cytokine, IL-15 has effects on both the innate immune system and the adaptive immune system. DiSabitino et al. (2011) *Cytokine Growth Factor Rev.* 22:19-33. Because it stimulates the proliferation and maintenance of many cells within the immune system that can fight against cells that appear to the host as foreign (or "non-self"), IL-15 has been proposed for use in the treatments of individuals suffering from cancer.

Thus, the present invention seeks to (among other things) identify a beneficial combination therapy involving an IL-2Rβ-selective agonist (also referred to herein as an IL-2Rβ-biased agonist) and an IL-15 agonist.

This and other needs in the art are addressed by the present invention. A number of aspects and embodiments are described herein. As such, each of the features and embodiments described herein, even if not explicitly stated, is meant to be applicable (but is not required to be applicable) to any other aspect, embodiment or feature or combination of features, unless stated to the contrary.

SUMMARY

In one or more aspects, a method is provided, the method comprising the steps of administering to a cancer patient: (a) an IL-2Rβ-activating amount of a long-acting IL-2Rβ-selective agonist; and (b) an IL-15R-activating amount of a long-acting IL-15 moiety. By way of clarity, with regard to the sequence of steps in accordance with this method, unless otherwise indicated, the method is not limited to the sequence of steps and step (a) can be performed before, after, or simultaneously with, performing step (b). In one or more embodiments, step (a) is performed prior to step (b).

In yet one or more further aspects, a composition is provided, the composition comprising an IL-2Rβ-activating amount of a long-acting IL-2Rβ-selective agonist and an IL-15R-activating amount of a long-acting IL-15 moiety.

In yet a further aspect, a kit is provided, the kit comprising a long-acting, IL-2Rβ-selective agonist and a long-acting IL-15 moiety, accompanied by instructions for use. Generally, the kit comprises an IL-2Rβ activating amount of the IL-2Rβ-selective agonist and an IL-15R-activating amount of the long-acting, IL-15 moiety. The IL-2Rβ-selective agonist and the long-acting IL-15 moiety may be provided in a single composition or alternatively, may be provided in separate containers with appropriate instructions for use, e.g., by a patient diagnosed with cancer.

Additional aspects and related embodiments are set forth in the following description and claims.

BRIEF DESCRIPTION OF THE DRAWINGS

FIG. 1A provides plots for study groups A, C, D, F, G, and H. FIG. 1B provides plots for study groups A, C, E, I, J, and K. FIG. 1C provides plots for study groups A, B, C, L, M, and N. Details of the study groups are described in Table 1.

FIG. 2A provides plots for study groups A, C, D, F, G, and H. FIG. 2B provides plots for study groups A, C, E, I, J, and K. FIG. 2C provides plots for study groups A, B, C, L, M, and N. Details of the study groups are described in Table 1.

DETAILED DESCRIPTION

As used in this specification, the singular forms "a," "an," and "the" include plural referents unless the context clearly dictates otherwise.

In describing and claiming the present invention, the following terminology will be used in accordance with the definitions described below.

"Water soluble, non-peptidic polymer" refers to a polymer that is at least 35% (by weight) soluble, preferably greater than 70% (by weight), and more preferably greater than 95% (by weight) soluble, in water at room temperature. Typically, an unfiltered aqueous preparation of a "water-soluble" polymer transmits at least 75%, more preferably at least 95%, of the amount of light transmitted by the same solution after filtering. It is most preferred, however, that the water-soluble polymer is at least 95% (by weight) soluble in water or completely soluble in water. With respect to being "non-peptidic," a polymer is non-peptidic when it has less than 35% (by weight) of amino acid residues.

The terms "monomer," "monomeric subunit" and "monomeric unit" are used interchangeably herein and refer to one of the basic structural units of a polymer. In the case of a homo-polymer, a single repeating structural unit forms the polymer. In the case of a co-polymer, two or more structural units are repeated—either in a pattern or randomly—to form the polymer. Preferred polymers used in connection with the present invention are homo-polymers. The water-soluble, non-peptidic polymer comprises one or more monomers serially attached to form a chain of monomers.

"PEG" or "polyethylene glycol," as used herein, is meant to encompass any water-soluble poly(ethylene oxide). Unless otherwise indicated, a "PEG polymer" or a polyethylene glycol is one in which substantially all (preferably all) monomeric subunits are ethylene oxide subunits, though, the polymer may contain distinct end capping moieties or functional groups, e.g., for reaction or conjugation. PEG polymers for use in the present invention will comprise one of the two following structures: "—(CH$_2$CH$_2$O)$_n$—" or "—(CH$_2$CH$_2$O)$_{n-1}$CH$_2$CH$_2$—," depending upon whether or not the terminal oxygen(s) has been displaced, e.g., during a synthetic transformation. As stated above, for the PEG polymers, the variable (n) ranges from about 3 to 4000 (unless stated otherwise), and the terminal groups and architecture of the overall PEG can vary.

"Branched," in reference to the geometry or overall structure of a polymer, refers to a polymer having two or more polymer "arms" extending from a branch point.

A "physiologically cleavable" or "hydrolyzable" or "degradable" bond is a relatively labile bond that reacts with water (i.e., is hydrolyzed) under physiological conditions. The tendency of a bond to hydrolyze in water may depend not only on the general type of linkage connecting two atoms within a given molecule but also on the substituents attached to these atoms. Appropriate hydrolytically unstable or weak linkages include but are not limited to carboxylate ester, phosphate ester, anhydrides, acetals, ketals, acyloxyalkyl ether, imines, orthoesters, peptides, oligonucleotides, thioesters, and carbonates.

An "enzymatically degradable linkage" means a linkage that is subject to degradation by one or more enzymes.

A "stable" linkage or bond refers to a chemical bond that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, amines, and the like. Generally, a stable linkage is one that exhibits a rate of hydrolysis of less than about 1-2% per day under physiological conditions. Hydrolysis rates of representative chemical bonds can be found in most standard chemistry textbooks.

"Substantially" or "essentially" means nearly totally or completely, for instance, 95% or greater, more preferably 97% or greater, still more preferably 98% or greater, even more preferably 99% or greater, yet still more preferably 99.9% or greater, with 99.99% or greater being most preferred, of some given quantity. That is to say, "substantially" or "essentially" means at a minimum, 95% or greater of some given quantity.

"Pharmaceutically acceptable excipient" or "pharmaceutically acceptable carrier" refers to a component that may be included in the pharmaceutical compositions provided herein and which causes no significant adverse toxicological effects to a patient.

The term "patient," refers to a living organism suffering from or prone to a condition that can be prevented or treated by administration of a compound or a combination of compounds, or composition as described herein, and includes both humans and animals.

The present disclosure is based, at least in part, on the discovery of a particularly beneficial therapeutic combination comprising a long-acting IL-2R agonist, and more specifically, an IL-2Rβ-selective agonist and a long-acting IL-15 agonist. Interestingly, it has been discovered that the foregoing immunotherapeutic combination, as exemplified in the accompanying examples, was notably more effective in increasing median survival in two different murine tumor models than either single long-acting agent and was also more effective than a combination of a long-acting IL-2Rβ agonist and native IL-15 (i.e., a non-long acting IL-15 agonist). Notably, the co-administration of a long-acting IL-15 agonist did not appear to dampen or suppress the immune-system activating-function of the long-acting IL-2Rβ selective agonist, but rather appeared to enhance its ability to fight cancer, e.g., by stimulating the production of CD8+ T cells and provide an increased CD8:regulatory T-cell ratio. See, for example, the supporting data provided herein in the Examples.

Turning now to the instant method, composition, kit, and related embodiments, as indicated above, in one or more aspects, provided herein (among other things) is a method of treating a patient suffering from a cancer. The method comprises the steps of: (a) administering to the patient an IL-2Rβ-activating amount of a long-acting, IL-2Rβ-selective agonist; and (b) administering to the patient an IL-15R-activating amount of a long-acting, IL-15 agonist. With respect to administering steps (a) and (b), these administering steps can be performed in either order (as well as simultaneously) and the method is not limited in this regard. In one or more related embodiments, administering step (a) is carried out before administering step (b). In yet one or more alternative embodiments, administering step (b) is carried out before administering step (a). In yet one or more further embodiments, both administering steps (a) and (b) are carried out simultaneously. In an instance in which the method involves simultaneous administration of the long-acting, IL-2Rβ-selective agonist and the long-acting, IL-15 agonist, the administering may be of separate compositions each comprising a therapeutic amount, i.e., an IL-2Rβ-activating amount (i.e., therapeutic amount) of a long-acting, IL-2Rβ-selective agonist or an IL-15R-activating amount (i.e., therapeutic amount) of a long-acting, IL-15 agonist, or may be of a single composition comprising both the long-acting, IL-2Rβ-selective agonist and the long-acting, IL-15 agonist, each in a therapeutically effective amount as described above. Further, in one or more embodiments, steps (a) and/or (b) will be administered repeatedly, over a course of treatment. Alternatively, in or more embodiments, steps (a) and (b) will be carried out only once. The long-acting, IL-2Rβ-selective agonist and the long-acting IL-15 agonist, when administered separately, may be, but are not necessarily administered according to the same administration (i.e., dosing) protocol. That is to say, one cycle of treatment may comprise administering the long acting IL-2Rβ-selective agonist one or multiple times, while a therapeutically effective dose of the long acting IL-15 agonist may be administered either more or less frequently than the long acting IL-2Rβ-selective agonist. In some embodiments, administering the long-acting IL-2Rβ-selective agonist prior to the long-acting IL-15 agonist is preferred.

The treatment method described herein is typically continued for as long as the clinician overseeing the patient's care deems the treatment method to be effective, i.e., that the patient is responding to treatment. Non-limiting parameters that indicate the treatment method is effective may include one or more of the following: tumor shrinkage (in terms of weight and/or volume and/or visual appearance); a decrease in the number of individual tumor colonies; tumor elimination; progression-free survival; appropriate response by a suitable tumor marker (if applicable), increased number of NK (natural killer) cells, increased number of T cells, increased number of memory T cells, and increased number of central memory T cells.

Exemplary lengths of time associated with the course of therapy in accordance with the claimed method include: about one week; two weeks; about three weeks; about four weeks; about five weeks; about six weeks; about seven weeks; about eight weeks; about nine weeks; about ten weeks; about eleven weeks; about twelve weeks; about thirteen weeks; about fourteen weeks; about fifteen weeks; about sixteen weeks; about seventeen weeks; about eighteen weeks; about nineteen weeks; about twenty weeks; about twenty-one weeks; about twenty-two weeks; about twenty-three weeks; about twenty four weeks; about seven months; about eight months; about nine months; about ten months; about eleven months; about twelve months; about thirteen months; about fourteen months; about fifteen months; about sixteen months; about seventeen months; about eighteen months; about nineteen months; about twenty months; about twenty one months; about twenty-two months; about twenty-three months; about twenty-four months; about thirty months; about three years; about four years; about five years; perpetual (e.g., ongoing maintenance therapy). The foregoing duration may be associated with one or multiple rounds/cycles of treatment.

With regard to the frequency of administering the long-acting, IL-2Rβ-selective agonist, one of ordinary skill in the art will be able to determine an appropriate frequency. For example, a clinician can decide to administer the long-acting, IL-2Rβ-selective agonist relatively infrequently (e.g., once every two weeks) and progressively shorten the period between dosings as tolerated by the patient. With regard to frequency of administering the long-acting, IL-15 agonist, the frequency for these agents can be determined in a similar fashion. In addition, as detailed information regarding some long-acting, IL-2Rβ-selective agonists and long-acting, IL-15 agonists is known (and, in some instances, is derived from use of the particular agonist in clinical testing), it is also possible to refer to the literature to obtain an appropriate frequency of administration (keeping in mind that some adjustment may be necessary in view of the combined effects of the treatment regimen).

In one or more additional aspects, a composition is provided, the composition comprising an IL-2Rβ-activating amount of a long-acting, IL-2Rβ-selective agonist and an IL-15R-activating amount of a long-acting, IL-15 moiety, the features of which will be described in greater detail below.

Additionally, provided herein is a kit comprising: an IL-2Rβ-activating amount of a long-acting IL-2Rβ-selective agonist; an IL-15R-activating amount of a long-acting IL-15 moiety; and instructions for use of the IL-2Rβ-selective agonist and the long-acting, IL-15 moiety, for example, for treating cancer. In one embodiment, the instructions describe administering an IL-2Rβ-activating amount of a long-acting IL-2Rβ-selective agonist and an IL-15R-activating amount of a long-acting IL-15 moiety, as described herein. Over at least one round or cycle of treatment, both the IL-2Rβ-selective agonist and the long acting IL-15 moiety are administered. For example, in one embodiment, the kit comprises a composition comprising an IL-2Rβ-activating amount of a long-acting, IL-2Rβ-selective agonist and an IL-15R-activating amount of a long-acting, IL-15 moiety, as described herein. In one or more related embodiments, the composition or combination comprises as active components only the long-acting, IL-2Rβ-selective agonist and the long-acting IL-15 agonist. In yet one or more further embodiments, the composition or combination includes one or more additional active agents. The kit may also contain the long-acting, IL-2Rβ-selective agonist and the long-acting IL-15 agonist in separate containers, to be administered as separate and distinct compositions. For example, each of the IL-2Rβ-selective agonist and the long-acting IL-15 agonist may be comprised within a pharmaceutically acceptable composition, e.g., comprising one or more pharmaceutically acceptable excipients, where each separate and distinct composition is housed in a container suitable for use. In certain embodiments, each of the long-acting interleukins is provided in a solid form suitable for reconstitution and subsequent administration in accordance with the accompanying instructions.

The methods, compositions, and kits described herein involve a long-acting, IL-2Rβ-selective agonist. In this regard, the invention is not limited to any specific long-acting, IL-2Rβ-selective agonist so long as the agonist exhibits a ratio of binding affinity for IL-2Rβ to binding affinity for IL-2Rαβ that is at least 5 times greater (more preferably at least 10 times greater) than that exhibited by IL-2. By way of example, it is possible to measure binding affinities against IL-2 as a standard. For example, the binding affinity of the exemplary long acting IL-2Rβ-selective agonist, RSLAIL-2, to IL-2Rα and IL-2Rβ was measured directly by surface plasmon resonance (Biacore T-100) and compared to that of clinically available IL-2 (aldesleukin). More specifically, antihuman antibody (Invitrogen) was coupled to the surface of a CM-5 sensor chip using EDC/NHS chemistry. Then either human IL-2Rα-Fc or IL-2Rβ-Fc fusion protein was used as the captured ligand over this surface. Serial dilutions of RSLAIL-2 were made in acetate buffer pH 4.5, starting at 5 mM. These dilutions were then allowed to bind to the ligands for 5 minutes, and the response units (RU) bound were plotted against concentration to determine EC50 values. The affinities of each isoform to each IL-2 receptor subtype was then calculated as fold change relative to those of IL-2.

In this regard, the RSLAIL-2 referenced in Example 1 of PCT Int. Pat. Appl. Pub. No. WO 2015/125159 exhibits about a 60-fold decrease in affinity to IL-2Rαβ relative to IL-2, but only about a 5-fold decrease in affinity to IL-2Rβ relative to IL-2—thereby indicating its selectivity or bias for the IL-2 beta receptor.

Non-limiting examples of long-acting, IL-2Rβ-selective agonists are described in PCT Int. Pat. Appl. Pub. Nos. WO 2012/065086 and WO 2015/125159. An exemplary long-acting, IL-2Rβ-selective agonist is RSLAIL-2 referenced in Example 1 of PCT Int. Pat. Appl. Pub. No. WO 2015/125159. In this regard, RSLAIL-2 is a composition comprising compounds encompassed by the following formula:

wherein IL-2 is a residue of IL-2 and "n" is an integer from about 3 to about 4000, and pharmaceutically acceptable salts thereof. In one or more embodiments, the composition contains no more than 25% (based on a molar amount), preferably no more than 10% (based on a molar amount), or more preferably no more than 5% (based on a molar amount), of compounds encompassed by the following formula wherein IL-2 is a residue of IL-2, "n" is an integer from about 3 to about 4000, "n'" is an integer selected from the group consisting of 1, 2, 3, 7 and >7, and pharmaceutically acceptable salts thereof. Additional exemplary compositions of RSLAIL-2 comprise compounds in accordance with the above formula wherein the polymer portion of the molecule, including both polyethylene glycol arms, has a weight average molecular weight in a range of from about 250 Daltons to about 90,000 Daltons. Additional suitable ranges include weight average molecular weights in a range selected from about 1,000 Daltons to about 60,000 Daltons, in a range of from about 5,000 Daltons to about 60,000 Daltons, in a range of about 10,000 Daltons to about 55,000 Daltons, in a range of from about 15,000 Daltons to about 50,000 Daltons, and in a range of from about 20,000 Daltons to about 50,000 Daltons.

Additional illustrative weight-average molecular weights for the polyethylene glycol polymer portion include about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 1,500 Daltons, about 2,000 Daltons, about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons.

The long-acting, IL-2Rβ-selective agonist and the long-acting IL-15 moiety may be in the form of a pharmaceutically-acceptable salt. Typically, such salts are formed by reaction with a pharmaceutically-acceptable acids or an acid equivalent. The term "pharmaceutically-acceptable salt" in this respect, will generally refer to the relatively non-toxic, inorganic and organic acid addition salts. These salts can be prepared in situ in the administration vehicle or the dosage form manufacturing process, or by separately reacting a long-acting interleukin as described herein with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "*Pharmaceutical Salts*", *J. Pharm. Sci.* 66:1-19). Thus, salts as described may be derived from inorganic acids such as hydrochloride, hydrobromic, sulfuric, sulfamic, phosphoric, nitric, and the like; or prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In reference to the foregoing IL-2Rβ-selective agonist, the term "IL-2" as used herein, refers to a moiety having human IL-2 activity. The term, 'residue', in the context of residue of IL-2, means the portion of the IL-2 molecule that remains following covalent attachment to a polymeric agent such as a polyethylene glycol, at one or more covalent attachment sites, as shown in the formula above. It will be understood that when the unmodified IL-2 is attached to a polymer such as polyethylene glycol, the IL-2 is slightly altered due to the presence of one or more covalent bonds associated with linkage to the polymer(s). This slightly altered form of the IL-2 attached to another molecule is referred to a "residue" of the IL-2.

For example, proteins having an amino acid sequence corresponding to any one of SEQ ID NOs: 1 through 4 described in International Patent Publication No. WO 2012/065086 are exemplary IL-2 proteins, as are any proteins or polypeptides substantially homologous thereto. The term substantially homologous means that a particular subject sequence, for example, a mutant sequence, varies from a reference sequence by one or more substitutions, deletions, or additions, the net effect of which does not result in an adverse functional dissimilarity between the reference and subject sequences. For the purposes herein, sequences having greater than 95 percent homology, equivalent biological activity (although not necessarily equivalent strength of biological activity), and equivalent expression characteristics are considered substantially homologous. For purposes of determining homology, truncation of the mature sequence should be disregarded. As used herein, the term "IL-2" includes such proteins modified deliberately, as for example, by site directed mutagenesis or accidentally through mutations. These terms also include analogs having from 1 to 6 additional glycosylation sites, analogs having at least one additional amino acid at the carboxy terminal end of the protein wherein the additional amino acid(s) includes at least one glycosylation site, and analogs having an amino acid sequence which includes at least one glycosylation site. The term includes both natural and recombinantly produced moieties. In addition, the IL-2 can be derived from human sources, animal sources, and plant sources. One exemplary IL-2 is recombinant IL-2 referred to as Aldesleukin.

The methods, compositions, and kits described herein additionally comprise a long-acting, IL-15 agonist. In this regard, the invention is not limited to any specific long-acting, IL-15 agonist so long as—following administration to the patient—the agonist exhibits IL-15 agonism in vivo for an amount of time that is longer than would be the case for administration of IL-15.

Non-limiting examples of long-acting, IL-15 agonists are described in PCT Int. Pat. Appl. Pub. No. WO 2015/153753. Such examples include the following:

wherein, for each structure, each IL-15 is a residue of IL-15, each (n) is an integer from about 3 to about 4000, and pharmaceutical acceptable salts thereof. In addition, although each of the foregoing structures in this paragraph are depicted in the monoPEGylated form, exemplary long-acting, IL-15 agonists include the corresponding diPEGylated, triPEGylated, quatroPEGylated, and higher PEGylated forms are included as well. Additional exemplary long acting IL-15 agonists comprise compounds in accordance with the above formulae wherein the polymer portion of the molecule, including both polyethylene glycol arms, has a weight average molecular weight in a range of from about 250 Daltons to about 90,000 Daltons. Additional suitable ranges include weight average molecular weights in a range selected from about 1,000 Daltons to about 60,000 Daltons, in a range of from about 5,000 Daltons to about 60,000 Daltons, in a range of about 10,000 Daltons to about 55,000 Daltons, in a range of from about 15,000 Daltons to about 50,000 Daltons, and in a range of from about 20,000 Daltons to about 50,000 Daltons.

Additional exemplary weight-average molecular weights for the polyethylene glycol polymer portion of the long-acting IL-15 agonist include about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 1,500 Daltons, about 2,000 Daltons, about 2,200 Daltons, about 2,500 Daltons, about 3,000 Daltons, about 4,000

Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons.

In reference to the long-acting IL-15 moiety, the term "IL-15" as used herein, refers to a peptide or protein moiety having human IL-15 activity. One of ordinary skill in the art can determine whether any given moiety has IL-15 activity. Representative proteins comprising an amino acid sequence corresponding to any one of SEQ ID NOs: 1 through 3 as provided in International Patent Publication No. WO 2015/153753 are exemplary IL-15 proteins, as is any protein or polypeptide substantially homologous thereto in accordance with the description provided above. As used herein, the term "IL-15" includes such peptides and proteins modified deliberately, as for example, by site directed mutagenesis or accidentally through mutations. This term also includes analogs having from 1 to 6 additional glycosylation sites, analogs having at least one additional amino acid at the carboxy terminal end of the peptide or protein wherein the additional amino acid(s) includes at least one glycosylation site, and analogs having an amino acid sequence which includes at least one glycosylation site. The term includes naturally, recombinantly and synthetically produced moieties.

Assays for determining whether a given compound can act as an IL-15 agonist can be determined through routine experimentation by one of ordinary skill in the art. Various methods for determining in vitro IL-15 agonist activity are described in the art. An exemplary approach is based on a pSTAT assay. Briefly, if an IL-15-dependent CTLL-2 cell is exposed to a test article having IL-15 activity, initiation of a signaling cascade results that includes the phosphorylation of STAT5 at tyrosine residue 694 (Tyr694) that can be quantitatively measured. Assay protocols and kits are known and include, for example, the MSD Phospho(Tyr694)/Total STATa,b Whole Cell Lysate Kit (Meso Scal Diagnostics, LLC, Gaithersburg, MD). For use herein, a proposed IL-15 moiety that exhibits a pSTAT5 $EC_{50}$ value of less than about 300 ng/mL (more preferably less than about 150 ng/mL) for at least one of 5 minutes or 10 minutes is considered an "IL-15 agonist" in connection with the present invention. It is preferred, however, that the IL-15 agonist used in the present invention is more potent (e.g., having a pSTAT5 $EC_{50}$ value of less than 150 ng/mL at one of at least 5 minutes or 10 minutes, such as less than about 1 ng/mL, and even more preferably less than about 0.5 ng/mL at at least one of 5 minutes or at 10 minutes). In one or more embodiments, it is preferred that the long-acting, IL-15 agonist retains IL-15Rα dependence.

A compound proposed to be a long-acting, IL-15 agonist will be determined to be long-acting in accordance with the present invention so long as—following administration to the patient—the agonist exhibits IL-15 agonism in vivo for an amount of time that is longer than would be the case for administration of IL-15. Conventional approaches, such as those involving radiolabeling a compound, administering it in vivo, and determining its clearance, can be used to determine whether the compound proposed to be a long-acting, IL-15 agonist is "long-acting" (i.e., has a clearance that is longer than that of IL-15 administered in the same in vivo system). For the purposes herein, the long acting nature of a long-acting IL-15 agonist or the long acting nature of an IL-2Rβ selective agonist is typically determined using flow cytometry to measure STAT5 phosphorylation in lymphocytes at various timepoints after administration of the agonist to be evaluated in mice. As a reference, the signal is lost by around 24 hours with IL-15 or IL-2, but is sustained for a period greater than that for a long-acting IL-15 or IL-2Rβ-selective agonist. As an illustration, the signal is sustained over several days for both the RSLAIL-2 and LAIL-15 version 1 and version 2 compositions.

In accordance with the methods, compositions, and kits described herein, the long-acting, IL-2Rβ-selective agonist is provided in an IL-2Rβ-activating amount. One of ordinary skill in the art can determine how much a given long-acting, IL-2Rβ-selective agonist is sufficient to provide clinically relevant agonistic activity at IL-2Rβ. For example, one of ordinary skill in the art can refer to the literature and/or administer a series of increasing amounts of the long-acting, IL-2Rβ-selective agonist and determine which amount or amounts provide clinically effective agonistic activity of IL-2Rβ. Alternatively, an activating amount of both the long acting IL-2Rβ-selective agonist and long acting IL-15 agonist can be determined using the in vivo STAT5 phosphorylation assay described above (determined in vivo following administration) where an amount sufficient to induce STAT5 phosphorylation in greater than 10% of NK cells at peak is considered to be an activating amount.

In one or more instances, however, the IL-2Rβ-activating amount is an amount encompassed by one or more of the following ranges expressed in amount of protein: from about 0.01 to 1 mg/kg; from about 0.01 mg/kg to about 0.1 mg/kg; from about 1 mg/kg to about 1000 mg/kg; from about 2 mg/kg to about 900 mg/kg; from about 3 mg/kg to about 800 mg/kg; from about 4 mg/kg to about 700 mg/kg; from about 5 mg/kg to about 600 mg/kg; from about 6 mg/kg to about 550 mg/kg; from about 7 mg/kg to about 500 mg/kg; from about 8 mg/kg to about 450 mg/kg; from about 9 mg/kg to about 400 mg/kg; from about 5 mg/kg to about 200 mg/kg; from about 2 mg/kg to about 150 mg/kg; from about 5 mg/kg to about 100 mg/kg; from about 10 mg/kg to about 100 mg/kg; and from about 10 mg/kg to about 60 mg/kg.

In accordance with the methods, compositions, and kits described herein, an IL-15R-activating amount of a long-acting, IL-15 agonist is provided. One of ordinary skill in the art can determine the quantity of a long-acting, IL-15 agonist that is sufficient to provide clinically relevant agonist activity at the IL-15 receptor ("IL-15R").

In one or more instances, however, the IL-15R activating amount is encompassed by one or more of the following ranges (amounts based on Il-15 content): from about 0.001 mg/kg to about 1000 mg/kg; from about 0.01 mg/kg to about 1000 mg/kg; from about 0.1 mg/kg to about 1000 mg/kg; from about 1 mg/kg to about 1000 mg/kg; from about 2 mg/kg to about 900 mg/kg; from about 3 mg/kg to about 800 mg/kg; from about 4 mg/kg to about 700 mg/kg; from about 5 mg/kg to about 600 mg/kg; from about 6 mg/kg to about 550 mg/kg; from about 7 mg/kg to about 500 mg/kg; from about 8 mg/kg to about 450 mg/kg; from about 9 mg/kg to about 400 mg/kg; from about 5 mg/kg to about 200 mg/kg; from about 2 mg/kg to about 150 mg/kg; from about 5 mg/kg to about 100 mg/kg; from about 10 mg/kg to about 100 mg/kg; and from about 10 mg/kg to about 60 mg/kg.

For confirmation, as used herein with regard to IL-15R-activating amounts of the of the long-acting, IL-15 agonist, the amount and extent of the activation can vary widely and the combination with the long-acting, IL-2Rβ-selective agonist can still be effective. For example, an amount of the long-acting, IL-15 agonist that only minimally activates IL-15R can still be an activating amount as used herein so long as the methods, compositions, and kits described herein enable a clinically meaningful response. So too, an amount of a long-acting, IL-2Rβ-selective agonist that exhibits only minimal agonist activity at IL-2Rβ for a sufficiently extended period of time can still be a long-acting, IL-2Rβ-selective agonist so long as the methods, compositions, and kits described herein enables a clinically meaningful response. In some instances, due to (for example) synergistic responses, minimal activation of the IL-15R pathway may only be required in the presence of the long-acting, IL-2Rβ-selective agonist. In still other instances, due to (for example) synergistic responses, only minimal agonist activity of IL-2Rβ may be required in the presence of IL-15R activation.

The actual dose provided in the methods, compositions, and kits described herein will vary depend upon the age, weight, and general condition of the subject as well as the severity of the condition being treated, the judgment of the health care professional, and compounds of the methods, compositions, and kits.

Figure 1A:
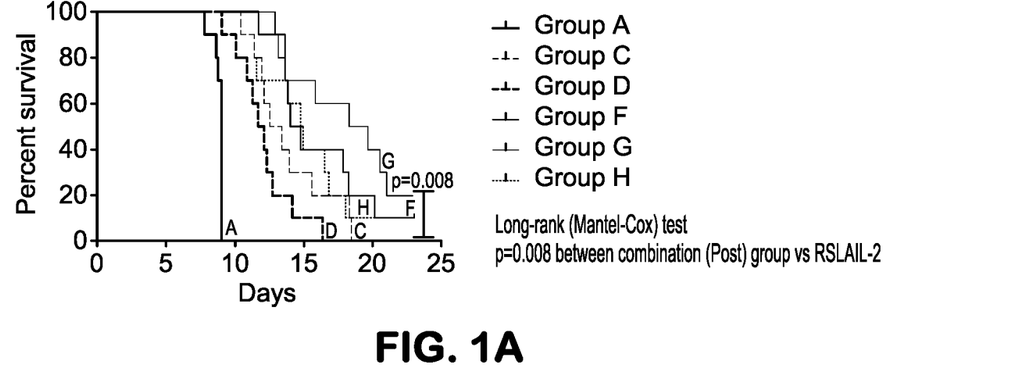
FIGS. 1A, 1B and 1C provide plots showing percent and days of survival of mice treated with various interventions in a mouse colon carcinoma model, which model and study is further described in Example 1.
Figure 1B:
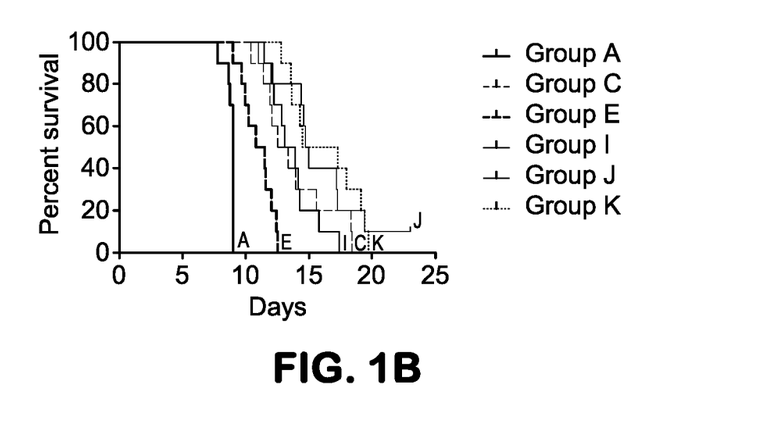
Figure 1C:
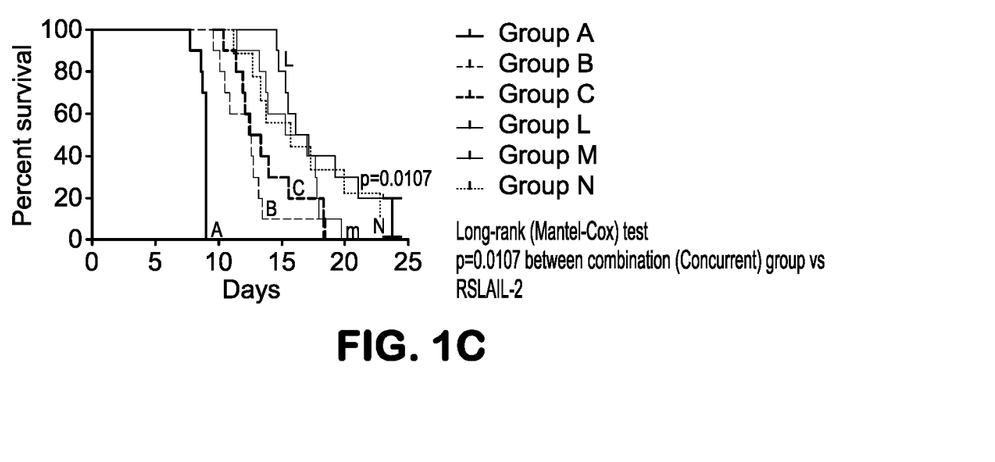

Data in support of the present combination, and it related methods, compositions, kits and the like, is provided in Example 1. Example 1 describes an evaluation of exemplary and certain preferred combinations of a long acting IL-2Rβ selective agonist and a long acting IL-15 agonist in mouse tumor models for both colon cancer and metastatic melanoma. More specifically, combinations of RSLAIL-2 with either LAIL-15 Version 1 or LAIL-15 Version 2 were evaluated in both a CT-26 mouse colon cancer model and in a mouse B16F10 metastatic melanoma model. Different administration protocols were examined, where variables included the dosing protocol, order of administration of the two long-acting cytokine compositions, and the particular long acting IL-15 agonist composition employed. Table 1 provides a summary of the different study groups and treatment schedules. Table 2 provides a summary of median survival for each of the study groups of mice bearing subcutaneous colon cancer tumors and treated in accordance with the combination and protocol described in Table 1. FIGS. 1A, 1B, and 1C are plots showing percent survival over time for each of the illustrative study groups. As can be seen, Group G exhibited significantly prolonged median survival over the corresponding group combining RSLAIL-2 with native (non-long acting) IL-15 (Group M), suggesting a particularly notable and beneficial effect for the illustrative combination of RSLAIL-2 and LAIL-15, Version 1 in treating a cancer such as colon cancer. In both models, the single long acting IL-2Rβ selective agonist, RSLAIL-2, appears to be more effective in inhibiting tumor growth than either of the LAIL-15 versions when administered singly (as controls), however, in certain combinations, LAIL-15 appears to be particularly effective in enhancing the anti-tumor effect of RSLAIL-2. Thus, rather than inhibiting the immunostimulatory cancer-fighting effect of RSLAIL-2, the addition of LAIL-15 appears to complement RSLAIL-2, perhaps due to the complementary mechanisms of immune activation of the two long acting cytokines. Similar results are seen in the metastatic melanoma mouse model as provided in Table 3. As can be seen, several treatment groups, F, G, I and J, exhibited significantly prolonged survival times when compared to each of the long-acting interleukins employed in the combination when administered as a single agent, and when compared to the corresponding combination of RSLAIL-2 with native (or non-long acting) IL-15. See also FIGS. 2A, 2B, and 2C. These results strongly suggest a synergistic interaction between the illustrative long-acting IL-2Rβ selective agonist, RSLAIL-2, and the long-acting IL-15 agonist exemplified by LAIL-15, Versions 1 and 2, pointing to the surprising efficacy of the subject immunotherapeutic combination for treating cancer.

The instant disclosure provides methods, compositions, and kits useful for (among other things) treating a patient suffering from a condition that is responsive to treatment with the compounds of the combination. For example, patients may be responsive to the individual agents alone as well as the combination of agents, but are more responsive to the combination of agents. By way of further example, patients may be non-responsive to one of the individual agents, but are responsive to the combination of agents. By way of still further example, patients may be non-responsive to either of the individual agents alone, but are responsive to the combination of agents.

In certain embodiments, the methods, compositions, and kits described herein are useful in delivering a therapeutically effective amount of active agents via injection. Other modes of administration are also contemplated, such as pulmonary, nasal, buccal, rectal, sublingual and transdermal. As used herein, the term "parenteral" includes subcutaneous, intravenous, intra-arterial, intraperitoneal, intracardiac, intrathecal, and intramuscular injection, as well as infusion injections. Each pharmacological component of the method can be administered separately. Alternatively, if administration of two pharmacological components is desired to be simultaneous—and the two pharmacological components are compatible together and in a given formulation—then the simultaneous administration can be achieved via administration of single dosage form/formulation (e.g., intravenous administration of an intravenous formulation that contains both pharmacologically active agents). For example, administration to a patient can be achieved through injection of composition comprising an IL-2Rβ-selective agonist and a diluent. In addition, administration to a patient can be achieved through injection of a composition comprising a long-acting, IL-15 agonist and a diluent. Further, administration can be achieved through injection of a composition comprising an IL-2Rβ-selective agonist, a long-acting, IL-15 agonist, and a diluent. With respect to possible diluents, the diluent can be selected from the group consisting of bacteriostatic water for injection, dextrose 5% in water, phosphate-buffered saline, Ringer's solution, lactated Ringer's solution, saline, sterile water, deionized water, and combinations thereof. One of ordinary skill in the art can determine through routing testing whether two given pharmacological components are compatible together in a given formulation.

The presently described methods, compositions, and kits can be used to treat a patient suffering from any condition that can be remedied or prevented by the methods, compositions, and kits. Exemplary conditions are cancers, such as, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell cancer, basal cell cancer, adenocarcinoma, sweat gland cancer, sebaceous gland cancer, papillary cancer, papillary adenocarcinomas, cystadenocarcinoma, medullary cancer, bronchogenic cancer, renal cell cancer, hepatoma, bile duct cancer, choriocarcinoma, seminoma, embryonal cancer, Wilms' tumor, cervical cancer, testicular cancer, lung cancer, small cell lung cancer, bladder cancer, epithelial cancer, glioma, astrocytoma, medulloblastoma, craniopharyngioma, ependymoma, pinealoma, hemangioblastoma, acoustic neuroma, oligodendroglioma, meningioma, melanoma (including, for example, uveal melanoma, mucosal melanoma, and leptomeningeal melanoma), neuroblastoma, retinoblastoma, and leukemias.

All articles, books, patents, patent publications and other publications referenced herein are incorporated by reference in their entireties. In the event of an inconsistency between the teachings of this specification and the art incorporated by reference, the meaning of the teachings and definitions in this specification shall prevail (particularly with respect to terms used in the claims appended herein). For example, where the present application and a publication incorporated by reference defines the same term differently, the definition of the term shall be preserved within the teachings of the document from which the definition is located.

EXAMPLES

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

The following materials were used in connection with examples provided herein.

"RSLAIL-2" refers to the composition obtainable upon following the procedures of Example 1 in PCT Int. Pat. Appl. Pub. No. WO 2015/125159, and generically is a composition comprising multiPEGylated forms of IL-2, wherein attachment of the PEG reagent used to form the conjugates is a releasable attachment following administration. RSLAIL-2 was prepared as follows. Purified rIL-2 (106.4 mL) at 1.44 mg/ml was charged into a first vessel followed by the addition of 53.6 mL of formulation buffer (10 mM sodium acetate, pH 4.5, 5% trehalose). The pH was measured at 4.62 the temperature was measured at 21.2° C. The PEG reagent, C2-PEG2-FMOC-NHS-20K (available as described in WO 2006/138572) (13.1 g), was charged into a second vessel followed by the addition of 73.3 mL of 2 mM HCl. The resulting solution was swirled by hand for 25 minutes. Sodium borate (0.5 M, pH 9.8) was added to the first vessel to raise the pH to about 9.1 and then the second vessel containing the PEG reagent was added to the first vessel over one to two minutes. A rinse step was then performed by charging 8.1 mL of 2 mM HCl into the second vessel and added to the first vessel. In the conjugation reaction, the final rIL-2 concentration was 0.6 mg/mL, the sodium borate concentration was 120 mM, the pH was 9.1+/−0.2, the temperature was 20-22° C., and the molar ratio of PEG reagent to rIL-2, after adjustment for activity of the reagent (substitution level) is 35:1. The conjugation reaction was allowed to proceed for thirty minutes and then was stopped with an acidification reaction using 75 mL of 2N acetic acid (where pH drops to 4.01). The product of the reaction was diluted with water and the diluted PEGylated rIL-2 solution was filtered using a 0.2 micron filter and the filtered product was placed in sterile containers.

The diluted PEGylated rIL-2 solution was purified by loading the solution onto a chromatography column packed with SP sepharose FF resin (GE Healthcare). Following a washing step, the PEGylated rIL-2 are eluted using a sodium chloride gradient. Fractions containing 1-mers, 2-mers or 3-mers are eliminated while fractions containing 4-mers, 5-mers, 6-mers, 7-mers and any higher degrees of PEGylation are pooled, thereby resulting in a composition having primarily 4-mers, 5-mers and 6-mers (wherein 8-mers and higher degrees of PEGylation were found to be removed during a washing step associated with chromatography). This resulting composition is "RSLAIL-2."

"LAIL-15 Version 1" refers to the composition obtainable upon following the procedures of Example 3 in PCT Int. Pat. Appl. Pub. No. WO 2015/153753, and generically is a composition comprising multiPEGylated forms of IL-15, wherein attachment of the PEG reagent used to form the conjugate is a releasable attachment following administration. The structure of "LAIL-15 Version 1," in a monoPEGylated form, is depicted below:

wherein IL-15 is a residue of native IL-15 and each "n" is an integer having a value such that the weight-average molecular weight of the polymeric reagent used to form the conjugate is about 20,000 Daltons. More specifically, "LAIL-15 Version 1" was prepared as follows. mPEG2-C2-fmoc-20K-NHS (the ~O—N-hydroxysuccinimidyl ester reactant prior to conjugation to IL-15), stored at −80° C. under argon, was warmed to ambient temperature under nitrogen purging. A stock solution (200 mg/mL) of mPEG2-C2-fmoc-20K-NHS was prepared in 2 mM HCl, and mPEG2-C2-fmoc-20K-NHS was added to the rIL-15 with molar ratios of mPEG$_2$-C2-fmoc-20K-NHS to rIL-15 ranging from 5:1 of 100:1. The final concentration of rIL-15 in the mixture was 0.5 mg/mL (0.031 mM). Sodium bicarbonate buffer (1 M, pH 8.0) was added to the mixture to reach a final concentration of 100 mM, and conjugation was allowed to proceed for thirty minutes to provide [mPEG2-C2-fmoc-20K]-[rIL-15] conjugates. After thirty minutes, quenching was achieved by adding 1 M glycine (pH 6.0) to the reaction mixture to achieve a final concentration of 100 mM. The pH of the quenched reaction mixture was then adjusted to 4.0 using glacial acetic acid prior to column chromatography purification and characterization.

"LAIL-15 Version 2" refers to the composition obtainable upon following the procedures of Example 4 in PCT Int. Pat. Appl. Pub. No. WO 2015/153753, and generically is a composition comprising multiPEGylated forms of IL-15, wherein attachment of the PEG reagent used to form the conjugate is a releasable attachment following administration. The structure of "LAIL-15 Version 2," in a monoPEGylated form, is depicted below:

wherein, IL-15 is a residue of native IL-15 and each (n) is an integer having a value such that the weight-average molecular weight of the polymeric reagent used to form the conjugate is about 20,000 Daltons. More specifically, "LAIL-15 Version 2" was prepared as follows. mPEG2-CAC-fmoc-20K-NHS (the ~O—N-hydroxysuccinimidyl ester reactant prior to conjugation to IL-15), stored at −80° C. under argon, was warmed to ambient temperature under nitrogen purging. A stock solution (200 mg/mL) of mPEG2-CAC-fmoc-20K-NHS was prepared in 2 mM HCl, and mPEG2-CAC-fmoc-20K-NHS was added to the rIL-15 with molar ratios of mPEG$_2$-CAC-fmoc-20K-NHS to rIL-15 ranged from 5:1 of 100:1. The final concentration of rIL-15 in the mixture was 0.5 mg/mL (0.031 mM). Sodium bicarbonate buffer (1 M, pH 8.0) was added to the mixture to reach a final concentration of 100 mM, and conjugation was allowed to proceed for thirty minutes to provide [mPEG2-CAC-fmoc-20K]-[rIL-15] conjugates. After thirty minutes, quenching was achieved by adding 1 M glycine (pH 6.0) to the reaction mixture to achieve a final concentration of 100 mM. The pH of the quenched reaction mixture was then adjusted to 4.0 using glacial acetic acid prior to column chromatography purification and characterization.

Example 1

Evaluation of Antitumor Activity of a Combination of RSLAIL-2 and Each of LAIL-15 Version 1 and Version 2 in CT26- and B16F10-Induced Subcutaneous Tumor Models of Balb/C and C57BL/6 Mice, Respectively Syngeneic tumors were induced in 6-8 week-old female Balb/C or C57BL/6 mice. Subcutaneously, into the postventral abdominal region, mouse colon cancer cells or metastatic melanoma cells were injected at a density of 2 or $1 \times 10^6$ cells mL$^{-1}$, respectively, in 100 μL volume of serum-free cell culture medium. Mice developed tumors of approximately 200 mm$^3$ for CT26 tumors, by 8-9 days, and 100 mm$^3$ for B16F10 tumors, by 6-7 days. Mice (Balb/C and C57BL/6 mice having either CT26 or B16F10 tumors separately) were divided into fourteen groups; each group consisted of ten animals. Each group was assigned one intervention, as follows: vehicle (Group A); native IL-15 alone (Group B); RSLAIL-2 alone (Group C); LAIL-15 Version 1 alone (Group D); LAIL-15 Version 2 alone (Group E); RSLAIL-2 sensitization and LAIL-15 Version 1: concurrent (Group F); RSLAIL-2 sensitization and LAIL-15 Version 1: post-sensitization (Group G); RSLAIL-2 sensitization and LAIL-15 Version 1: pre-sensitization (Group H); RSLAIL-2 sensitization and LAIL-15 Version 2: concurrent (Group I); RSLAIL-2 sensitization and LAIL-15 Version 2: post-sensitization (Group J); RSLAIL-2 sensitization and LAIL-15 Version 1: pre-sensitization (Group K); RSLAIL-2 sensitization and native IL-15: concurrent (Group L); RSLAIL-2 sensitization and native IL-15: post-sensitization (Group M); and RSLAIL-2 sensitization and native IL-15: pre-sensitization (Group N). Table 1 provides a summary of the study groups and treatment schedules used for each of the two models.

TABLE 1

Study Groups and Treatment Schedules for Treating Mouse Colon Cancer (CT-26) or Metastatic Melanoma (B16F10) With Tested Interventions

| Group (N = 10) | Intervention | Dose in mpk | Route | Treatment day & Schedule |
|---|---|---|---|---|
| A | vehicle | — | ip | q5dx3 |
| B | native IL-15 | 0.3 | ip | q2dx6 |
| C | RSLAIL-2 | 0.8 | iv | q1d (Day0) |
| D | LAIL-15 Version 1 | 0.3 | iv | q5dx3 |

TABLE 1-continued

Study Groups and Treatment Schedules for Treating Mouse Colon Cancer (CT-26) or Metastatic Melanoma (B16F10) With Tested Interventions

| Group (N = 10) | Intervention | Dose in mpk | Route | Treatment day & Schedule |
|---|---|---|---|---|
| E | LAIL-15 Version 2 | 0.3 | iv | q5dx3 |
| F | RSLAIL-2 sensitization + LAIL-15 Version 1: concurrent | 0.8 + 0.3 | iv | RSLAIL-2: (q1d) (Day 0) LAIL-15 Version 1: (q5dx3) (Day 0, 5, 10) |
| G | RSLAIL-2 sensitization + LAIL-15 Version 1: post-sensitization | 0.8 + 0.3 | iv | RSLIAL-2: (q1d) (Day 0) LAIL-15 Version 1: (q5dx3) (Day 5, 10, 15) |
| H | RSLAIL-2 sensitization + LAIL-15 Version 1: pre-sensitization | 0.8 + 0.3 | iv | RSLAIL-2: (q1d) (Day 5) LAIL-15 Version 1: (q5dx3) (Day 0, 5, 10) |
| I | RSLAIL-2 sensitization + LAIL-15 Version 2: concurrent | 0.8 + 0.3 | iv | RSLAIL-2: (q1d) (Day 0) LAIL-15 Version 2: (q5dx3) (Day 0, 5, 10) |
| J | RSLAIL-2 sensitization + LAIL-15 Version 2: post-sensitization | 0.8 + 0.3 | iv | RSLAIL-2: (q1d) (Day 0) LAIL-15 Version 2: (q5dx3) (Day 5, 10, 15) |
| K | RSLAIL-2 sensitization + LAIL-15 Version 2: pre-sensitization | 0.8 + 0.3 | iv | RSLAIL-2: (q1d) (Day 5) LAIL-15 Version 2: (q5dx3) (Day 0, 5, 10) |
| L | RSLAIL-2 sensitization + native IL-15: concurrent | 0.8 + 0.3 | iv/ip | RSLAIL-2: (q1d) (Day0) Parent IL-15: (q2dx6) (Day 0, 2, 4, 6, 8, 10) |
| M | RSLAIL-2 sensitization + native IL-15: post-sensitization | 0.8 + 0.3 | iv/ip | RSLAIL-2: (q1d) (Day0) Parent IL-15: (q2dx6) (Day 5, 7, 9, 11, 13, 15) |
| N | RSLAIL-2 sensitization + native IL-15: pre-sensitization | 0.8 + 0.3 | iv/ip | RSLAIL-2: (q1d) (Day5) Parent IL-15: (q2dx6) (Day 0, 2, 4, 6, 8, 10) |

Following administration of the intervention, mice were measured for changes in growth of subcutaneous colon cancer or metastatic melanoma tumors, as appropriate, by digital calipers, thrice a week. Daily clinical signs were also monitored.

In subcutaneous colon tumor-bearing mice, as shown in FIGS. 1A, 1B and 1C, the vehicle control reached the study end point by day 9 while all other groups continued.

Furthermore, as shown in Table 2, the median survival for all treatment groups in comparison to vehicle is found to be statistically significant via a Log-rank (Mantel-Cox) test. In particular, the combination of RSLAIL-2 and LAIL-15 Version 1 in approach described for "Group G" exhibited significant median survival over RSLAIL-2 alone, suggesting a synergistic effect.

TABLE 2

Median Survival for Interventions Groups in CT-26 Subcutaneous Tumor-Bearing Mice

| Group (N = 10) | Intervention | Median Survival (Days) |
|---|---|---|
| A | vehicle | 9 |
| B | native IL-15 | 12.48**** |
| C | RSLAIL-2 | 12.96**** |
| D | LAIL-15 Version 1 | 11.90**** |
| E | LAIL-15 Version 2 | 11.16*** |
| F | RSLAIL-2 sensitization + LAIL-15 Version 1: concurrent | 14.39**** |
| G | RSLAIL-2 sensitization + LAIL-15 Version 1: post-sensitization | 18.97****$$ |
| H | RSLAIL-2 sensitization + LAIL-15 Version 1: pre-sensitization | 14.85**** |
| I | RSLAIL-2 sensitization + LAIL-15 Version 2: concurrent | 13.51**** |
| J | RSLAIL-2 sensitization + LAIL-15 Version 2: post-sensitization | 14.87**** |
| K | RSLAIL-2 sensitization + LAIL-15 Version 2: pre-sensitization | 15.91**** |
| L | RSLAIL-2 sensitization + native IL-15: concurrent | 16.63****$ |
| M | RSLAIL-2 sensitization + native IL-15: post-sensitization | 16.12**** |
| N | RSLAIL-2 sensitization + native IL-15: pre-sensitization | 15.72**** |

Log-rank (Mantel-Cox) test;
***$p < 0.001$ and
****$p < 0.0001$ vs. vehicle;
$$p < 0.05$ and
$$$p < 0.01$ vs individual treatment with RSLAIL-2.

Moreover, all pharmacologically active interventions groups were well-tolerated, with mice showing neither significant decrease in body weight or deleterious clinical signs.

Figure 2A:
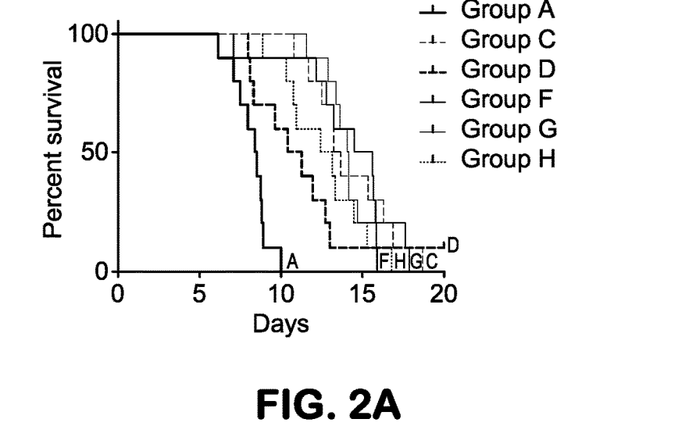
FIGS. 2A, 2B and 2C provide plots showing percent and days of survival of mice treated with various interventions in a mouse metastatic melanoma model, which model and study is further described in Example 1.
Figure 2B:
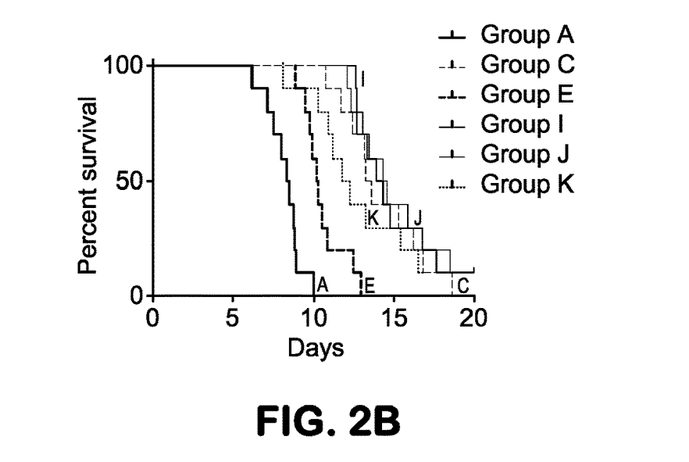
Figure 2C:
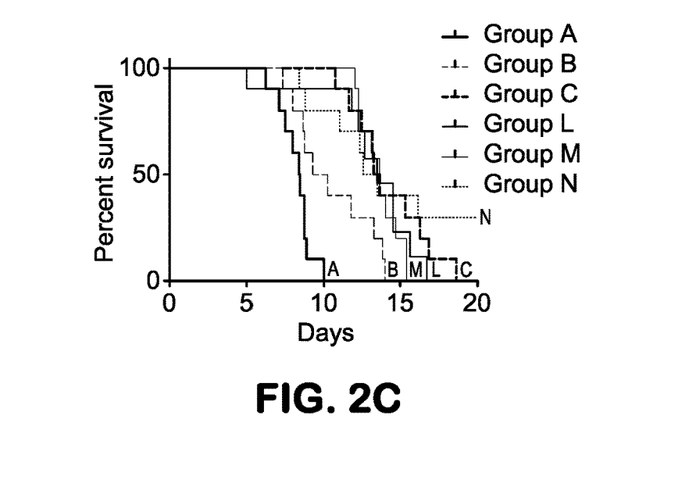

In subcutaneous metastatic melanoma tumor-bearing mice, as shown in FIGS. 2A, 2B and 2C, the vehicle control reached the study end point by day 10 while all other groups continued.

Furthermore, as shown in Table 3, the median survival for all treatment groups in comparison to vehicle is found to be statistically significant via a Log-rank (Mantel-Cox) test.

TABLE 3

Median Survival for Interventions Groups in Metastatic Melanoma (B16F10) Subcutaneous Tumor-Bearing Mice

| Group (N = 10) | Intervention | Median Survival (Days) |
|---|---|---|
| A | vehicle | 8.44 |
| B | native IL-15 | 9.80* |
| C | RSLAIL-2 | 13.46****^ |
| D | LAIL-15 Version 1 | 10.84* |
| E | LAIL-15 Version 2 | 10.26**** |
| F | RSLAIL-2 sensitization + LAIL-15 Version 1: concurrent | 15.04**** |
| G | RSLAIL-2 sensitization + LAIL-15 Version 1: post-sensitization | 14.09**** |
| H | RSLAIL-2 sensitization + LAIL-15 Version 1: pre-sensitization | 12.80**** |
| I | RSLAIL-2 sensitization + LAIL-15 Version 2: concurrent | 14.16****#### |
| J | RSLAIL-2 sensitization + LAIL-15 Version 2: post-sensitization | 14.45****#### |
| K | RSLAIL-2 sensitization + LAIL-15 Version 2: pre-sensitization | 12.02**** |
| L | RSLAIL-2 sensitization + native IL-15: concurrent | 13.53****^ |
| M | RSLAIL-2 sensitization + native IL-15: post-sensitization | 13.69****^ |
| N | RSLAIL-2 sensitization + native IL-15: pre-sensitization | 13.09***^ |

Log rank (Mantel-Cox test);
*$p = 0.05$, and
****$p < 0.0001$ vs vehicle;
^$p < 0.045$ vs native IL-15 alone;
$p < 0.05$,
$p < 0.0001$ vs individual treatment of LAIL-15 Version 2.

Mice treated with native IL-15, LAIL-15 Version 1, LAIL-15 Version 2, and RSLAIL-2 have shown neither significant decrease in body weight nor deleterious clinical signs. However, administration of combination of RSLAIL-2 and LAIL-15 Version 1 (pre- and concurrent sensitization) exhibited a decrease in average body weight by ~10% by day 5. The decreased body weights regained by day 7, indicating reversible nature.

Example 2

Evaluation of Antitumor Activity of a Combination of RSLAIL-2 and LAIL-15 Version 2 in an Alternative Subcutaneous Tumor Model in Mice

A combination of RSLAIL-2 and LAIL-15 Version 2 was evaluated in a tumor model in mice which differs from the tumor model of Example 1. The combination of RSLAIL-2 and LAIL-15 Version 2 was evaluated for efficacy against new and established tumors. For both new and established tumors, the combination of RSLAIL-2 and LAIL-15 Version 2 was effective in reducing tumor size.

The number, and relevant ratios, of certain immune system cells were increased following administration of the combination of RSLAIL-2 and LAIL-15 Version 2 in the new and established mouse tumor models.

These results suggest the combination of RSLAIL-2 and LAIL-15 Version 2 is a promising potential immunoncology treatment.

What is claimed is:

1. A method of treating a patient suffering from a cancer, the method comprising the steps of:
   (a) administering to the patient an IL-2Rβ-activating amount of a long-acting, IL-2Rβ-selective agonist comprised of an IL-2 moiety covalently attached to a water-soluble polymer having the formula:

wherein each n is an integer from 3 to 4000, or pharmaceutically acceptable salts thereof; and (b) administering an IL-15 receptor-activating amount of a long-acting IL-15 agonist comprised of an IL-15 protein covalently attached to at least one water-soluble polymer having a formula selected from:

and wherein n for each formula is an integer from 3 to 4000, or pharmaceutically acceptable salts thereof.

2. The method of claim 1, wherein the patient is human.

3. The method of claim 1, wherein the cancer is a solid cancer.

4. The method of claim 1, wherein the solid cancer is selected from the group consisting of breast cancer, ovarian cancer, colon cancer, prostate cancer, colorectal cancer, gastric cancer, malignant melanoma, liver cancer, small cell lung cancer, non-small cell lung cancer, thyroid cancers, kidney cancer, cancer of the bile duct, brain cancer, cervical cancer, maxillary sinus cancer, bladder cancer, esophageal cancer, Hodgkin's disease and adrenocortical cancer.

5. The method of claim 3, wherein the cancer is colon cancer.

6. The method of claim 3, wherein the cancer is breast cancer.

7. The method of claim 1, wherein step (a) is carried out prior to step (b) being carried out.

8. The method of claim 1, wherein (a) is carried out after step (b) is carried out.

9. The method of claim 1, wherein steps (a) and (b) are carried out simultaneously.

10. The method of claim 1, wherein the IL-2 moiety is aldesleukin.

11. The method of claim 1, wherein the polymer portion of the IL-2Rβ-selective agonist, including both poly(ethylene glycol) arms, has a weight-average molecular weight in a range of from 250 daltons to 90,000 daltons.

12. The method of claim 1, wherein the polymer portion of the IL-2Rβ-selective agonist, including both poly(ethylene glycol) arms, has a weight-average molecular weight of 20,000 daltons.

13. The method of claim 1, wherein n is selected such that the polymer portion of the IL-15 agonist, including both poly(ethylene glycol) arms, has a weight average molecular weight in a range of from 20,000 daltons to 90,000 daltons.

14. The method of claim 1, wherein one, two, or three water-soluble polymers are attached to the IL-15 protein.

* * * * *